(12) United States Patent
Kiselev et al.

(10) Patent No.: US 8,791,150 B2
(45) Date of Patent: Jul. 29, 2014

(54) PHARMACEUTICAL COMPOSITION FOR PERORAL ADMINISTRATION OF DIINDOLYLMETHANE

(75) Inventors: Vsevolod Ivanovich Kiselev, Moscow (RU); Irina Gennadievna Vassilieva, Moscow (RU)

(73) Assignee: Zakrytoe Aktsionernoe Obschestvo "Veles Farma", Moscow (RU)

( * ) Notice: Subject to any disclaimer, the term of this patent is extended or adjusted under 35 U.S.C. 154(b) by 123 days.

(21) Appl. No.: 13/377,261

(22) PCT Filed: Sep. 7, 2010

(86) PCT No.: PCT/RU2010/000487
§ 371 (c)(1),
(2), (4) Date: Dec. 9, 2011

(87) PCT Pub. No.: WO2011/034465
PCT Pub. Date: Mar. 24, 2011

(65) Prior Publication Data
US 2013/0065933 A1      Mar. 14, 2013

(30) Foreign Application Priority Data
Sep. 18, 2009   (RU) ............................... 2009134872

(51) Int. Cl.
*A01N 43/38* (2006.01)
*A61K 9/14* (2006.01)
*A61K 9/00* (2006.01)

(52) U.S. Cl.
USPC ............................ 514/414; 424/486; 424/400

(58) Field of Classification Search
None
See application file for complete search history.

(56) References Cited

U.S. PATENT DOCUMENTS

| 6,277,410 B1 | 8/2001 | Kabanov et al. |
| 6,416,793 B1 | 7/2002 | Zeligs et al. |
| 2005/0267193 A1 * | 12/2005 | Zeligs ........................... 514/414 |

FOREIGN PATENT DOCUMENTS

| RU | 2 318 509 C2 | | 3/2008 |
| WO | WO 2009/114525 | * | 9/2009 |

OTHER PUBLICATIONS

ApplicChem, Pluronic F-68, accessed May 20, 2013, p. 1.*
Dai, Wei-Guo, et al., International Journal of Pharmaceutics, 355 (2008), pp. 31-37.*
International Search Report for PCT/RU2010/000487 dated Feb. 10, 2011.

* cited by examiner

*Primary Examiner* — Scott Long
*Assistant Examiner* — Lyndsey Beckhardt
(74) *Attorney, Agent, or Firm* — Birch, Stewart, Kolasch & Birch, LLP

(57) ABSTRACT

Block copolymer pharmaceutical compositions containing 3,3'-diindolylmethane (DIM). The pharmaceutical composition for peroral administration comprises 3,3'-diindolylmethane as an active component and a target additive, the target additive being a block copolymer of oxyethylene and oxypropylene, in which the content of the hydrophobic oxypropylene block is less than 50 mass % and the molecular mass of the hydrophilic oxyethylene block is equal to 2,250 Da or more, at a ratio of the active component to the selected block copolymer varying between 1:2 and 1:10. The composition improves absorption of the active compound by the bloodstream upon peroral delivery.

3 Claims, 4 Drawing Sheets

PHARMACEUTICAL COMPOSITION FOR PERORAL ADMINISTRATION OF DIINDOLYLMETHANE

This application is the U.S. national phase under 35 U.S.C. §371 of PCT/RU2010/000487 (filed Sep. 7, 2010) and this application claims priority to Russian patent application 2009-134872, filed Sep. 18, 2009.

FIELD OF THE INVENTION

The invention relates to pharmacy, in particular, to new pharmaceutical compositions for peroral administration of 3,3'-diindolylmethane (DIM) and to methods for treating diseases with the help thereof.

BACKGROUND OF THE INVENTION 3,3'-diindolylmethane (DIM), and its analogues and derivatives have a broad spectrum of biological activities for which reason DIM may be regarded as a pharmacologically active compound of great promise. 3,3-diindolylmethane (DIM) is the main oligomer product of indole-3-carbinol (I3C) proved to be highly selective is respect of transformed cells of varied origin (Aggarwal B. B., Ichikawa H. (2005), Molecular Targets and Anticancer Potential of Indole-3-Carbinol and Its Derivatives, *Cell Cycle*, 4(9), 1201-1215). Pharmacokinetic studies have shown that perorally administered I3C is almost immediately transformed to DIM in the acidic medium of the stomach (Arneson D. W., Hurwitz A., McMahon L. M., Robaugh D. (1999), Presence of 3,3'-Diindolylmethane in Human Plasma after Oral Administration of Indole-3-Carbinol (Abstr.), *Proc. Am. Assoc. Cancer Res.*, 40, 2833). Many researchers studying anticancer activity of I3C tend, therefore, to accept the idea that a majority of clinical effects registered upon its administration are actually produced by the dimer form of indole-3-carbinol, or DIM.

It has been demonstrated experimentally that nearly all multiple anticancer mechanisms induced by I3C in vitro and in vivo are inherent in DIM as well (Chang X., Tou J. C., Hong C., et al. (2005), 3,3'-Diindolylmethane Inhibits Angiogenesis and the Growth of Transplantable Human Breast Carcinoma in Athymic Mice, *Carcinogenesis*, 264(4), 771-778; Firestone G. L., Bjeldanes L. F. (2003), Indole-3-Carbinol and 3,3-Diindolylmethane Anti-Proliferative Signaling Pathways Control Cell Cycle Gene Transcription in Human Breast Cancer Cells by Regulating Promoter-Sp1 Transcription Factor Interactions, *J. Nutr.*, 133, 2448S-2455S; Ge X., Yannai S., Rennert G., et al. (1996), 3,3'-Diindolylmethane Induces Apoptosis in Human Cancer Cells, *Biochem. Biophys. Res. Commun.*, 228, 153-158; Hong C., Kim H. A., Firestone G. L., et al. (2002), 3,3'-Diindolylmethane (DIM) Induces a Cell Cycle Arrest in Human Breast Cancer Cells That Is Accompanied by Sp-1-Mediated Activation of p21 WAF1/CIP1 Expression, *Carcinogenesis*, 23, 1297-1305; Leibelt D. A., Hedstrom O. R, Fisher K. A. (2003), Evaluation of Chronic Dietary Exposure to Indole-3-Carbinol and Absorption Enhanced 3,3'-Diindolylmethane in Sprague-Dawley Rats, *Toxicol. Sci.*, 74, 10-21; Li Y., Li X., Sarkar F. H. (2003), Gene Expression Profiles of I3C- and DIM-Treated PC3 Human Prostate Cancer Cells Determined by cDNA Microarray Analysis, *J. Nutr.*, 133, 1011-1019; Nachshon-Kedmi M., Yannai S., Haj A., Fares F. A. (2003), Indole-3-Carbinol and 3,3'-Diindolylmethane Induces Apoptosis in Human Prostate Cancer Cells, *Food Chem. Toxicol.*, 41, 745-752). This conclusion applies to prostate cancer as well. Like I3I, DIM in vitro and in vivo inhibits growth of prostate cancer cells (Li Y., Li X., Sarkar F. H. (2003), Gene Expression Profiles of I3C- and DIM-Treated PC3 Human Prostate Cancer Cells Determined by cDNA Microarray Analysis, *J. Nutr.*, 133, 1011-1019; Nachshon-Kedmi M., Fares F. A., Yannai S. (2004), Therapeutic Activity of 3,3'-Diindolylmethane on Prostate Cancer in an in vivo Model, *Prostate*, 61 (2), 153-160) and induces their apoptosis (Li Y., Li X., Sarkar F. H. (2003), Gene Expression Profiles of I3C- and DIM-Treated PC3 Human Prostate Cancer Cells Determined by cDNA Microarray Analysis, *J. Nutr.*, 133, 1011-1019; Nachshon-Kedmi M., Yannai S., Fares F. A. (2004), Induction of Apoptosis in Human Prostate Cancer Cell Line, PC3, by 3,3'-Diindolylmethane Through the Mitochondrial Pathway, *Br. J. Cancer*, 91, 1358-1363), in which case it, similarly to I3C, displays its activity at the submolecular level by regulating the expression of genes responsible for proliferation, differentiation, and survivability processes (Li Y., Li X., Sarkar F. H. (2003), Gene Expression Profiles of I3C- and DIM-Treated PC3 Human Prostate Cancer Cells Determined by cDNA Microarray Analysis, *J. Nutr.*, 133, 1011-1019) and inhibiting multiple signaling pathways leading to cellular hyperproliferation.

The hormone-sensitive prostate cells (culture LNCaP) have been used to demonstrate that DIM can be bound concurrently to androgen receptors to suppress in this way their translocation into the nucleus and successive activation of gene transcription, and also expression of the gene promoter encoding the prostate-specific PSA antigen. The PSA protein (specific prostate protease) is a classical marker of prostate cancer that is produced and secreted in abundance by prostate cancel cells. The same paper established, after structural studies undertaken, that DIM is very similar in molecular geometry to the well-known synthetic anti-androgen Casodex (Le H. T, Schaldach C. M., Bjeldanes L. F. (2003), Plant-Derived 3,3'-Diindolylmethane Is a Strong Androgen Antagonist in Human Prostate Cancer Cells, *J. Biol. Chem.*, 278, 21136-21145) that, in contrast to DIM, however, promotes translocation of androgen receptors into the nucleus (Masiello D., Cheng S., Bubley G. J., et al. (2002), Bicalutamide Functions as an Androgen Receptor Antagonist by Assembly of a Transcriptionally Inactive Receptor, *J. Biol. Chem.*, 277, 26321-26326).

The capacity of DIM to display anti-angiogenic activity, discovered only recently, is an extremely significant development. Pathological growth of vessels almost always accompanies hyper- and neoplastic processes. It is common knowledge that unless a network of capillary vessels is formed to supply oxygen and nutrients to a new tumor of 1 to 2 mm in diameter the tumor would not continue to grow at all. It has been demonstrated that micromolar concentrations of DIM in vitro suppress proliferation and migration of endothelial cells and their capacity to form vessels effectively. In vivo, DIM injected subcutaneously to experimental animal (5 mg/kg daily) was 74% effective in suppressing pathological neoangiogenesis (Chang X., Tou J. C., Hong C., et al. (2005), 3,3'-Diindolylmethane Inhibits Angiogenesis and the Growth of Transplantable Human Breast Carcinoma in Athymic Mice, *Carcinogenesis*, 264(4), 771-778; McCarty M. F., Block K. I. (2005), Multifocal Angiostatic Therapy: An Update, *Integrative Cancer Therapies*, 4(4), 301-314).

The nuclear transcription factor NF-κB is the most significant molecular target displaying an activity that modern target preparations (directional preparations) developed and adopted in clinical practice are intended to block. It has been proved that this factor mediates the inflammatory response and has a key role in regulating proliferative (anti-apoptotic), angiogenic, migratory, and invasive cellular activities at the final stage of signaling pathways induced by growth factors and cytokines. Moreover, translocation of the active factor into the nucleus and transcription activation of genes responsible for these processes is a significant event. It has been found that, if used in vitro, DIM (Rahman K. M., Ali S., Aboukameel A., et al. (2007), Inactivation of NF-KappaB by 3,3'-Diindolylmethane Contributes to Increased Apoptosis Induced by Chemotherapeutic Agent in Breast Cancer Cells, *Mol. Cancer Ther.*, 6(10), 2757-2765; Rahman K. M., Sarkar F. H. (2005), Inhibition of Nuclear Translocation of Nuclear Factor-κB Contributes to 3,3'-Diindolylmethane-Induced Apoptosis in Breast Cancer Cells, *Cancer Res.*, 65, 364-371) and its metabolic predecessor I3C are effective in suppressing nuclear translocation and activity of NF-κB. This means that, in addition to its anti-proliferative and anti-angiogenic effect, the DIM-base preparation is capable of suppressing local inflammatory reactions that frequently attend hyper- and neoplastic processes in hormone-dependent organs and tissues.

A detailed study of patients with regression of cervical dysplasias conducted within the framework of placebo-controlled clinical research has helped trace a direct link between the positive dynamics of the disease and the efficiency of I3C conversion to DIM (Sepkovic D. W., Bradlow H. L., Bell M. (2001), Quantitative Determination of 3,3'-Diindolylmethane in the Urine of Individuals Receiving Indole-3-Carbinol, *Natr. Cancer*, 41, 57-63). The high DIM concentration was determined in the urine of patients receiving the preparation.

One of the most recent experimental studies demonstrated the capacity of DIM to induce apoptosis of human cervical HPV-infected keratinocytes in vitro. Moreover, in one of the three cellular cervical cancer lines studied, DIM displayed a much higher efficiency than I3I. The value of $LD_{50}$ was 50 to 60 μM for DIM and 200 μM for I3C, respectively, but, unlike its metabolic predecessor (I3C), DIM did not induce any apoptotic changes in normal (untransformed) keratinocytes (Chen D. Z., Qi M., Auborn K., Carter T. H. (2001), Indole-3-Carbinol and Diindolylmethane Induce Apoptosis of Human Cervical Cancer Cells and in Murine HPV16-Transgenic Preneoplastic Cervical Epithelium, *J. Nutrit.*, I3I, 3294-3302).

To conclude, DIM has been discovered recently to have yet another property, perhaps one of its most important advantages—its immunomodulating activity. The researchers have shown that when used in vitro DIM stimulates IFNγ-dependent signaling pathways in tumor cells by activating expression of IFNγ receptors, and also other IFN-responsive regulatory proteins.

The peroral method of dosing DIM-base preparations must be given preference because it offers a series of advantages over other dosing methods, in particular, patient comfort, flexible treatment tactics, and treatment costs. Peroral dosing, however, limits significantly the biological availability of DIM because of its poor solubility and low absorption efficiency in the small intestines. DIM typically shows poor solubility in physiological salt solutions and has a limited capacity to pass through barrier membranes. Furthermore, this compound is known to be bound to blood plasma proteins and be involved in various unspecific reactions in the bloodstream that reduce greatly the efficiency of its delivery to the disease focus.

Several pharmaceutical compositions based on pegylated vitamin E (TPGS) have been developed recently as a way to dispose of the above-mentioned problems (Anderton M. J., Manson M. M., et al. (2004), Physiological Modeling of Formulated and Crystalline Diindolylmethane Pharmacokinetics Following Oral Administration in Mice, *Drug Metabolism and Disposition*, 32(6), 632-638). Pegylated vitamin E is known for its capacity to enhance solubility of various compounds in water (Constantinides P. P., Tustian A., Kessler D. R. (2004), Tocol Emulsions for Drug Solubilization and Parenteral Delivery, *Adv. Drug Deliv. Rev.*, 56, 1243-1255) and improve their biological availability when administered perorally (Wu S. H. W., Hopkins W. K. (1999), Characteristics of d-α-Tocopheryl PEG 1000 Succinate for Applications as an Absorption Enhancer in Drug Delivery Systems, *Pharm. Technol.*, 23, 52-68). TPGS-base compositions, however, can increase insignificantly only (by 50% to 100% only) the biological availability of DIM, and its analogues and derivatives (Zeligs, et al., U.S. Pat. No. 6,416,793, Formulation and Use of Controlled-Release Indole Alkaloids), for which reason the therapeutic potential of these compounds cannot be utilized in full.

SUMMARY OF THE INVENTION

It is an object of this invention, therefore, to improve DIM delivery.

This object is achieved by a new pharmaceutical composition for peroral delivery of DIM on the basis of block copolymers of oxyethylene and oxypropylene.

The pharmaceutical composition for peroral administration comprises 3,3'-diindolylmethane as an active component and a target additive, which is a block copolymer of oxyethylene and oxypropylene, in which the content of the hydrophobic block is less than 50 mass %, and the hydrophilic block has a molecular mass of 2,250 Da or more, at a ratio of the active component to the selected block copolymer equal to between 1:2 and 1:10.

The pharmaceutical composition preferably contains Pluronic F127 copolymer as a block copolymer of oxyethylene and oxypropylene.

The pharmaceutical composition may further contain Pluronic L10.

The pharmaceutical composition may further contain a pharmaceutically acceptable carrier.

The pharmaceutical composition may be in the form of a tablet, lyophilized powder, suspension, or a capsule.

Figure 1:
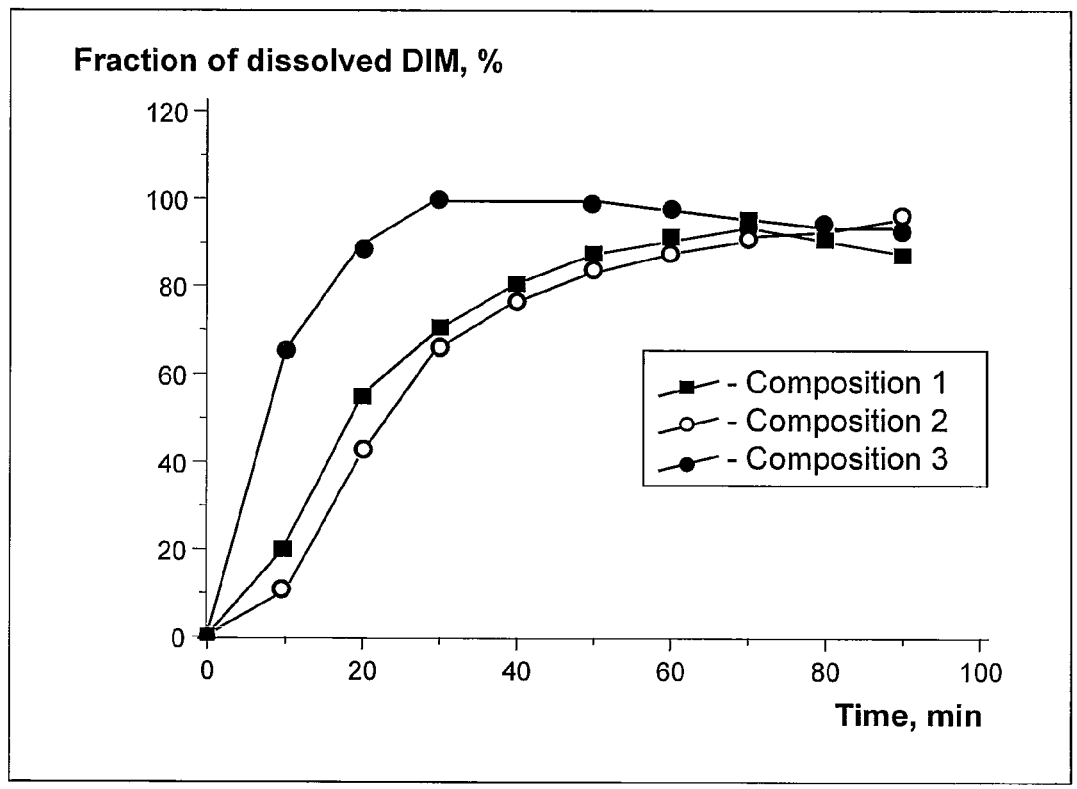
FIG. 1 illustrates dynamics of DIM dissolution (DIM concentration is determined from changes in optical density).
Composition 1—DIM (control);
Composition 2—Pluronic F127 and DIM;
Composition 3—Pluronic F127, Pluronic L10, and DIM.

Group I (4 patients) was given the claimed DIM-base pharmaceutical composition; and Group II (4 patients) was given a pharmaceutical composition containing crystalline DIM.

DESCRIPTION OF THE PREFERRED EMBODIMENTS OF THE INVENTION

The block copolymers of oxyethylene and oxypropylene are also known under the name of Pluronic and Poloxamer.

The hydrophobic-hydrophilic properties of Pluronics and their capacity to solubilize water-insoluble compounds are determined from the size and proportions of the polyoxyethylene (hydrophilic) and polyoxypropylene (hydrophobic) blocks. The following table (Table 1) shows the structural properties of various Pluronics.

TABLE 1

Structural Properties of Various Pluronics

| Pluronic | Mass of hydrophilic block, Da | Content of hydrophobic block, mass % |
|---|---|---|
| L10 | 3,200 | 60% |
| L31 | 950 | 90% |
| F35 | 950 | 50% |
| L42 | 1,200 | 80% |
| L43 | 1,200 | 70% |
| L44 | 1,200 | 60% |
| L61 | 1,750 | 90% |
| L62 | 1,750 | 80% |
| L63 | 1,750 | 70% |
| P65 | 1,750 | 50% |
| F68 | 1,750 | 20% |
| L72 | 2,050 | 80% |
| P75 | 2,050 | 50% |
| L81 | 2,250 | 90% |
| P84 | 2,250 | 60% |
| P85 | 2,250 | 50% |
| F87 | 2,250 | 30% |
| F88 | 2,250 | 20% |
| L92 | 2,750 | 80% |
| F98 | 2,750 | 20% |
| P103 | 3,250 | 70% |
| P104 | 3,250 | 60% |
| P105 | 3,250 | 50% |
| F108 | 3,250 | 20% |
| L121 | 4,000 | 90% |
| L122 | 4,000 | 80% |
| L123 | 4,000 | 70% |
| F127 | 4,000 | 30% |
| 10R5 | 1,000 | 50% |
| 10R8 | 1,000 | 20% |
| 12R3 | 1,200 | 70% |
| 17R2 | 1,700 | 80% |
| 17R2 | 1,700 | 80% |
| 17R4 | 1,700 | 60% |
| 17R8 | 1,700 | 20% |
| 22R4 | 2,200 | 60% |
| 25R1 | 2,500 | 90% |
| 25R2 | 2,500 | 80% |
| 25R4 | 2,500 | 60% |
| 25R5 | 2,500 | 50% |
| 25R8 | 2,500 | 50% |
| 31R1 | 3,100 | 90% |
| 31R2 | 3,100 | 80% |
| 31R4 | 3,100 | 60% |

Although the above block copolymers are used widely in pharmaceutical and cosmetic compositions, for example, for enhancing the solubility of hydrophobic water-insoluble compounds (Foster B., Cosgrove T., Hammouda B. (2009), Pluronic Triblock Copolymer Systems and Their Interactions with Ibuprofen, *Langmuir*, 25(12), 6760-6766), individualized approach to their use is needed for each specific drug.

More than fifty ATP-dependent transporters capable of influencing, in one way or another, the biological availability of drugs are known today (Oostendorp R. L., Beijnen J. H., Schellens J. H. (2009), The Biological and Clinical Role of Drug Transporters at the Intestinal Barrier, *Cancer Treat. Rev.*, 35(2), 137-147). Moreover, the genetic polymorphism of these transporters also contributes significantly to the variability of bioavailability of different drugs (Nakamura T., Yamamori M., Sakaeda T. (2008), Pharmacogenetics of Intestinal Absorption, *Curr. Drug Deliv.*, 5(3), 153-169). The exact mechanisms of interaction between various surface-active polymers and various transporters and their combinations that restrict the bioavailability of different drugs have not yet been established, and a composition having a positive effect on the bioavailability of one active agent may be ineffective for another agent, and conversely.

Oral bioavailability of compounds enhanced by block copolymers of oxyethylene and oxypropylene is related to modulation of P-glycoprotein activity and, accordingly, these block copolymers are suggested for addition to compositions in which P-glycoprotein substrates are the active agents (Kabanov A. V. et al., U.S. Pat. No. 6,277,410, Copolymer Compositions for Oral Delivery), as are several MRP formulations (Miller D. W., Batrakova E. V., Kabanov A. V. (1999), Inhibition of Multidrug Resistance-Associated Protein (MRP) Functional Activity with Pluronic Block Copolymers, *Pharm. Res.*, 16(3), 396-401). Similar properties were demonstrated for other surface-active polymer compounds. In particular, in addition to high solubilizing activity in respect of water-insoluble compounds, the capacity of Solutol H15 to modulate activity of P-glycoprotein was established (Coon J. S., Knudson W., Clodfelter K., et al. (1991), Solutol HS 15, Nontoxic Polyoxyethylene Esters of 12-Hydroxystearic Acid, Reverses Multidrug Resistance, *Cancer Res.*, 51, 897-902), making it potentially capable of being used as an absorption enhancer of peroral drug formulations. Similar properties were also revealed in Chremophor EL, Tween 80, TPGS referred to above, and other similar compounds (Seelig A., Gerebtzoff G. (2006), Enhancement of Drug Absorption by Noncharged Detergents Through Membrane and P-Glycoprotein Binding, *Expert Opinion on Drug Metabolism and Toxicology*, 2(5), 733-752).

A direct experiment described below (Example 8) has shown that DIM does not enhance the capture of rhodamine 123 by cells expressing P-glycoprotein, which is an indication that DIM is not a substrate of that transporter. This finding agrees well with the results of the above-mentioned attempt to use TPGS as a highly active P-glycoprotein modulator for enhancing DIM bioavailability, an attempt that failed to enhance this parameter significantly. In comparison, a number of surface-active polymers used in accordance with this invention have led to a significant enhancement of oral bioavailability of the drug.

An analysis of DIM solubility in Pluronics containing different proportions of hydrophobic and hydrophilic blocks has shown that polymers containing 50 mass % or more of the hydrophilic block have a higher solubilizing capacity than polymers containing less than 50 mass % of the hydrophilic block. Some Pluronics are known to have a constant molecular mass of the hydrophilic element and a variable content of oxyethylene groups.

It was discovered unexpectedly that DIM bioavailability also depends on the molecular mass of the hydrophilic block. The higher bioavailability is contributed by block copolymers of oxyethylene and oxypropylene in which the content of the hydrophobic block is under 50 mass % and the molecular mass of the hydrophilic block is 2,250 Da or more. Pluronic F127 displays the highest efficiency and can be used to obtain stable water dispersions containing over 3 mg/ml of DIM.

When this DIM composition was administered perorally to rats its biological availability increased significantly (more than fivefold). The proportions of the active component and selected block copolymer may be varied depending on the desired release time and averages between 1:2 and 1:10. The most optimal ratio of DIM to Pluronic F127 is 1:6.

It was also found unexpectedly that Pluronic L10 (containing about 40% of the hydrophilic block and about 3,200 in total molecular mass), that had little effect on DIM solubility in water and biological availability upon peroral administration to rats, proved to be capable of enhancing significantly the effect of Pluronic F127 and increasing the bioavailability of the DIM formulation more than 15-fold against control. The optimal ratio of Pluronic F127 to Pluronic L10 was found to be within 8:1 to 1:1. It was also a surprise that other Pluronics containing under 50% of the hydrophilic block, for example, Pluronic P85 and Pluronic L61, did not produce a similar effect.

Compositions of the invention may be produced, for example, by joint or separate dissolution of components in suitable solvents such as water, and alcohol or water-alcohol solutions, followed by mixing the solutions in required proportions.

The resultant solutions may not necessarily be dried to produce a solid drug formulation. Solutions are dried by any technically suitable method or a combination of methods, including, but not limited to, methods such as evaporation in a rotary vaporizer or SpeedVac, lyophilic drying, or continuous flow drying.

Ready drug formulations may be obtained by tabletizing dried compositions with the use of necessary excipients, for example, sodium stearate, lactose, cellulose derivatives, and so on.

Ready drug formulations may be obtained by packing dried compositions into capsules, for example, gelatin capsules having solid shells.

Pharmaceutical compositions containing an effective quantity of DIM may be used to treat various diseases.

Considering the above-mentioned molecular targets of DIM, in particular, its positive effect on the metabolism of estrogens, restoration of apoptotic processes, and anti-proliferative, antitumor, and anti-angiogenic activity, the compositions described herein are suitable for treating proliferative diseases such as uterine myoma, adenomyosis, and hyperplastic prostate diseases. We have also demonstrated the high clinical efficiency of high bioavailability DIM in treatment of infectious diseases of the urogenital tract caused by intracellular infectious agents such as *Chlamydia trachomatis*. Most probably, these effects are caused by induction of programmed cellular death of epithelial cells infected by *Chlamydia trachomatis*.

The effective quantity of 3,3'-diindolylmethane needed for treatment and disease prevention may vary depending on the kind and severity of disease and the patient's age and condition, and can be determined by the doctor in charge on a case to case basis. The doses used vary within 2 mg to 2,000 mg a day.

The invention is illustrated with the following examples:

EXAMPLE 1

Determination of DIM Solubility in Aqueous Dispersions of Various Pluronics

Preparation of Pluronic Solution 400 mg of Pluronic, 9.7 ml of dehydrated ethyl alcohol, and 0.3 ml of distilled water were placed in a glass container. The resultant mixture was stirred carefully in a magnetic mixer until a transparent solution was obtained.

Preparation of DIM Solution 10 mg of DIM was put in a glass container, and 1.0 ml of dehydrated ethyl alcohol was added. The mixture was stirred carefully in a magnetic mixer until a transparent solution was obtained.

Preparation of Molecular Dispersions Containing Pluronic and DIM 0.5 ml of Pluronic solution (20 mg) and 0.2 ml of DIM solution were placed in a 2 ml test tube. The resultant solution was treated with ultrasound for 10 minutes and stirred for 1 hour. Ethanol was removed from the resultant mixture in a rotary vaporizer or SpeedVac, and evaporation continued in vacuum overnight. As a result of these processes, the resultant mixture was dissolved in 1.5 ml of distilled water and filtered, and DIM concentration in the resultant solution was determined by the spectrometric method. The results given in the following table (Table 2) show that DIM had the highest solubility when Pluronic F127 was used.

TABLE 2

DIM Solubility in Aqueous Dispersions of Various Pluronics

| Pluronic | Mass of hydrophilic blocks | Content of hydrophobic blocks | DIM solubility in water, mg/ml |
|---|---|---|---|
| L10 | 1,000 | 60% | >0.01 |
| L31 | 950 | 90% | >0.01 |
| F35 | 950 | 50% | 0.15 |
| L42 | 1,200 | 80% | >0.01 |
| L43 | 1,200 | 70% | >0.01 |
| L44 | 1,200 | 60% | 0.1 |
| L61 | 1,750 | 90% | >0.01 |
| L62 | 1,750 | 80% | >0.01 |
| L63 | 1,750 | 70% | >0.01 |
| P65 | 1,750 | 50% | 0.2 |
| F68 | 1,750 | 20% | 0.35 |
| L72 | 2,050 | 80% | >0.01 |
| P75 | 2,050 | 50% | 0.33 |
| L81 | 2,250 | 90% | >0.01 |
| P84 | 2,250 | 60% | 0.15 |
| P85 | 2,250 | 50% | 1.2 |
| F87 | 2,250 | 30% | 0.9 |
| F88 | 2,250 | 20% | 0.8 |
| L92 | 2,750 | 80% | >0.01 |
| F98 | 2,750 | 20% | 0.4 |
| P103 | 3,250 | 70% | >0.01 |
| P104 | 3,250 | 60% | 0.3 |
| P105 | 3,250 | 50% | 0.5 |
| F108 | 3,250 | 20% | 0.5 |
| L121 | 4,000 | 90% | >0.01 |
| L122 | 4,000 | 80% | >0.01 |
| L123 | 4,000 | 70% | 0.02 |
| F127 | 4,000 | 30% | <3.0 |

EXAMPLE 2

Preparation of Molecular Suspensions Containing Pluronic F127 and DIM

Preparation of Pluronic F127 Solution 400 mg of Pluronic F127, 9.7 ml of dehydrated ethyl alcohol, and 0.3 ml of distilled water were placed in a glass container. The resultant mixture was carefully stirred in a magnetic mixer until a transparent solution was obtained.

Preparation of DIM Solution 10 mg of DIM were placed in a glass container and 1.0 ml of dehydrated ethyl alcohol was added. The content was carefully stirred in a magnetic mixer until a transparent solution was obtained.

Preparation of Molecular Suspensions Containing Pluronic F127 and DIM 0.5 ml of Pluronic F127 solution (20 mg) and 0.2 ml of DIM solution were placed in a 2 ml test tube. The resultant solution was treated with ultrasound for 10 minutes and stirred for 1 hour. Ethanol was removed from the resultant mixture in a rotary vaporizer or SpeedVac, and evaporation continued in vacuum overnight. As a result of these processes, a wax-like mass was obtained to be dissolved in distilled water to a target DIM concentration of 3 mg in 1 ml of distilled water.

EXAMPLE 3

Preparation of Molecular Suspensions Containing Pluronic F127, Pluronic L10, and DIM Preparation of Pluronic L10 Solution 250 mg of Pluronic L10 and 10 ml of dehydrated ethyl alcohol were placed in a glass container. The resultant mixture was carefully stirred in a magnetic mixer.

Preparation of Pluronic F127 Solution 400 mg of Pluronic F127, 9.7 ml of dehydrated ethyl alcohol, and 0.3 ml of distilled water were placed in a glass container. The resultant mixture was carefully stirred in a magnetic mixer until a transparent solution was obtained.

Preparation of DIM Solution 10 mg of DIM were placed in a glass container and 1.0 ml of dehydrated ethyl alcohol was added. The content was carefully stirred in a magnetic mixer until a transparent solution was obtained.

Preparation of Molecular Suspensions Containing Pluronic F127, Pluronic L10, and DIM 0.5 ml of Pluronic F127 solution (20 mg), 0.2 ml of DIM solution, and 0.1 ml of Pluronic L10 solution were placed in a 2 ml test tube. The resultant solution was treated with ultrasound for 10 minutes and stirred for 1 hour. Ethanol was removed from the resultant mixture in a rotary vaporizer or SpeedVac, and evaporation continued in vacuum overnight. As a result of these processes, a wax-like mass was obtained, to be dissolved in distilled water to a target DIM concentration of 3 mg per 1 ml of distilled water.

EXAMPLE 4

Preparation of Water-soluble DIM Composition by Lyophilization 1 ml of distilled water was added to one of the DIM solutions containing Pluronics described in Examples 1 and 2. The mixture was stirred in a mixer until a transparent solution was obtained. The solution was stable for 15 hours. The resultant solution was frozen and placed in a lyophilic drier. Lyophilization of the frozen solution produced colorless powder.

EXAMPLE 5

Preparation of DIM Composition by Spray Drying 200 g of Pluronic F127, 300 ml of distilled water, and 10 liters of ethanol were placed in a 20-liter glass container. The mixture was stirred until the Pluronic was dissolved completely and a transparent solution was obtained. 25 g of Pluronic L10 and 20 g of DIM were added to the resultant solution. The resultant mixture was stirred until a transparent solution was obtained and was filtered thereafter. The resultant solution was dried in a spray drier at a temperature of 40° C.

EXAMPLE 6

Preparation of a Composition by Dissolving DIM Directly in Molten Pluronics

Pluronic F98 and Pluronic F127, or a combination thereof in an optimal proportion (F98 to F127 at approximately 1:4), were mixed and melted (at 60° C.), whereupon crystalline DIM was added to the molten mass at vigorous stirring. After DIM was dissolved, the solution was cooled rapidly to +5° C. The resultant solid mass was ground to powder.

EXAMPLE 7

Study of the Solubility of DIM-containing Compositions

The study was done to determine the solubility of DIM compositions obtained in Examples 2 and 3 in water. For this purpose, 2 ml of 0.9% aqueous solution of sodium chloride was added to each of the resultant compositions (buttons thereof contained 6 mg of DIM each) and placed in a horizontal shaker rotating at 200 revolutions per minute. 0.2 ml samples were taken periodically to determined DIM concentration from changes in the optical density thereof. The results of the experiments are shown in the drawing (FIG. 1).

EXAMPLE 8

Study of the Inhibiting Activity of Dim Relative to Membrane P-glycoprotein

Absorption of rhodamine (Rhodamine 123 (R123) by MESSA/DX cells expressing membrane P-glycoprotein (P-gp) was studied as a model for experiments to be conducted. Negative P-gp MESSA/DX cells were used as control. The cells were placed in a 96-well plate at a concentration of 40,000 cells per well. After 24 hour of incubation, R123 at a concentration of 3 μM was added to the cells and incubation continued for 1 hour at 37° C. in the presence of various concentrations of DIM and verapamil, a well-known P-gp inhibitor. At the end of incubation, the solution was removed and the cells were rinsed three times with a cooled phosphate buffer. Rhodamine fluorescence was then measured in the cell samples. All the experiments were run three times. As was expected, MESSA/DX cells expressing membrane P-gp absorbed rhodamine insignificantly in comparison with negative MESSA cells. Verapamil, a well-known P-gp inhibitor, increases R123 accumulation in MESSA/DX cells depending on dose, but does not affect R123 accumulation in any of the cell lines, which definitely means that DIM is not a substrate for P-gp.

EXAMPLE 9

Pharmacokinetics of DIM in Experimental Animals Given Dim Compositions

DIM compositions prepared as in Examples 3 to 4 were used for the purposes of this study. The results are given in the table at the end of this example.

The compositions were administered to animals perorally in the form of aqueous dispersions at a target DIM concentration of 3 mg in 1 ml of solvent. Crystalline DIM was administered as a suspension of 15 mg of DIM in 5 ml of 0.5% methylcellulose in distilled water.

Spraque-Dawley female rats weighing 250 to 350 g were used in the experiment. All the experiments were conducted strictly in accordance with the GLP rules. DIM formulations were administered to the animals at 60 mg per 1 kg of body weight. Blood samples were withdrawn at different time intervals (15, 30, 45 minutes and 1, 2, 4, 6, and 24 hours) after drug administration. The blood samples were centrifuged immediately after withdrawal, and the plasma separated from blood was frozen and stored at −80° C.

Isofluran (Bimeta-MTC, Animal Health Inc., Cambridge, ON, Canada). Blood was drawn from the jugular vein into heparin-containing test tubes that were placed immediately on ice for 5 to 10 minutes. The blood was then centrifuged to separate it from plasma. Plasma samples were frozen and stored at −80° C.

Sample Extraction and Analysis

Plasma samples were unfrozen, centrifuged, and 100 µl aliquots were packed in plastics test tubes. The samples were then extracted twice with 750 µl of methyl-tert-butyl ester for 2 minutes while stirring at 180° C. The samples were centrifuged at 10,000 r.p.m. for 10 minutes. The supernatants were separated and transferred to glass test tubes. The organic phase was evaporated by nitrogen at 50° C. until it was completely dry. The dried samples were stored at −80° C. The samples studied were dissolved in 15 µl of acetonitrile and 85 µl of mobile phase. The aliquots of a total volume of 20 µl were then analyzed by the HPLC method.

HPLC Performance:

$C_{18}$ reverse-phase columns 50×4.6 mm, Symmetry/shield 3.5 µm (sorbent, grains in µm), 30° C., flow speed 1.5 ml/min., injection volume 20 µl, at 280 nm.

Mobile phase: Linear gradient of buffer B, from 0% to 100%, buffer A: 5% acetonitrile, 0.1% trifluoroacetic acid, buffer B: 90% acetonitrile, 0.1% trifluoroacetic acid, for 10 minutes.

Figure 2:
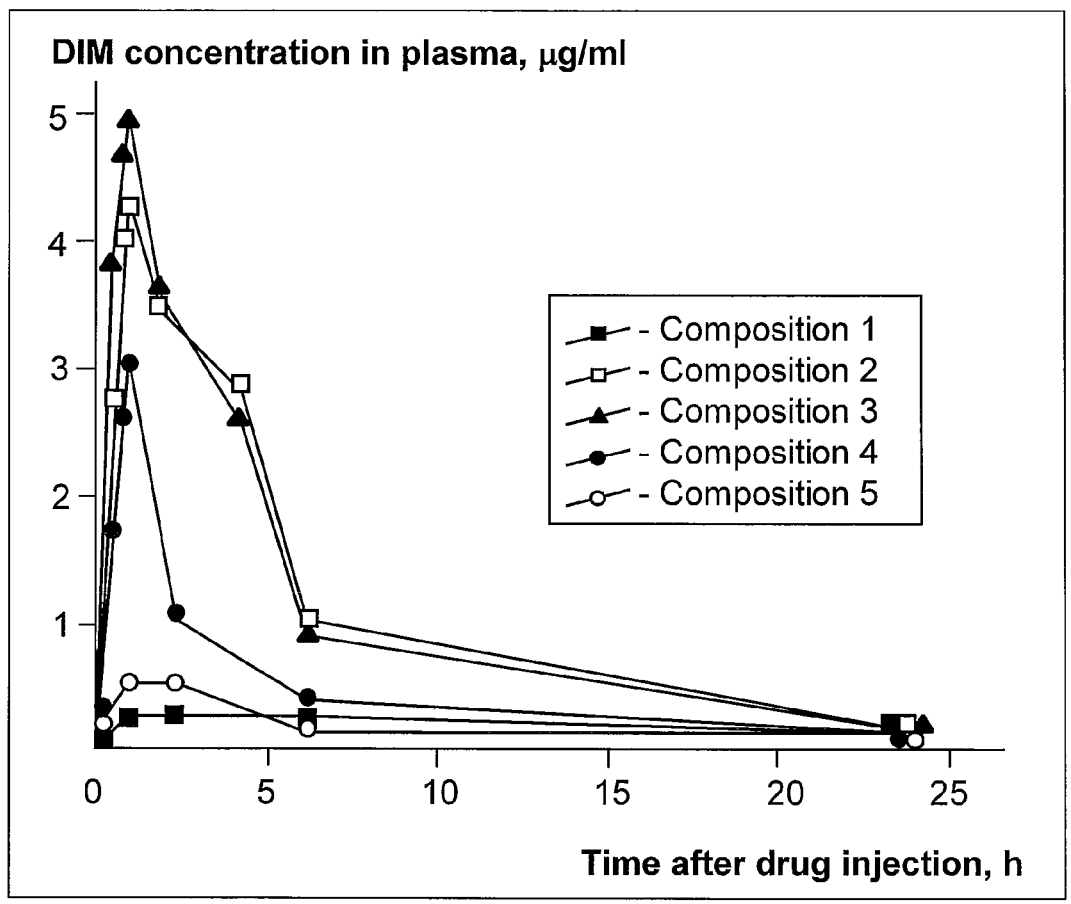
FIG. 2 illustrates pharmacokinetics of DIM in the plasma of rats given the following compositions:
Composition 1—DIM (control);
Composition 2—Pluronic F127 and DIM;
Composition 3—lyophilically dried solution of Pluronic F127, Pluronic L10, and DIM.
Composition 4—Pluronic F127 and DIM;
Composition 5—Pluronic L10 and DIM.

DIM concentration was determined on a calibration curve, on the basis of peak area (AUP). The area under the curves (AUC) was determined from the trapezoidal rule (which is used to determine specific integrals). The values of $C_{max}$ and AUC for control and compositions are given in the following table (Table 3):

The data are presented graphically in the following drawing (see: FIG. 2) illustrating pharmacokinetics of DIM in the plasma of rats given the above compositions.

EXAMPLE 10

Study of Clinical Efficiency of Pharmaceutical DIM Composition of Example 2

Purpose of the Study

The study was done to assess the clinical efficiency, morphological effects, and safety of the new pharmaceutical DIM composition (containing 50 mg of 3,3'-diindolylmethane in a capsule) in comparison with a pharmaceutical composition containing crystalline DIM (50 mg of crystalline DIM in a capsule).

The objects of the study were to:

Assess the effect of the preparations on the dynamics of dysfunction symptoms of the lower urinary tracts and the quality of life of prostate adenoma patients;

Assess the effect of the preparations on the principal urodynamic factors: maximum urine flow rate ($Q_{max}$) and residual urine volume ($V_{res}$);

Assess the effect of the preparations on PSA dynamics;

Assess the effect of the preparations on prostate volume;

Assess the nature of morphological effects on prostate tissue in comparison with placebo; and Assess the safety of the preparations on the basis of an analysis of the frequency of undesirable events, side effects, and dynamics of the principal biochemical parameters of blood serum.

Tests were conducted with:

A pharmaceutical composition containing DIM in accordance with the invention (Group I), 2 capsules/twice a day.

A pharmaceutical composition containing crystalline DIM (Group II), 2 capsules/twice a day.

Thirty-four patients with prostate gland adenoma (PGA) and prostate intraepithelial neoplasia (PIN) were examined and treated to assess the clinical efficiency, morphological effects, and safety of the preparations. Group I (18 patients) were given 2 capsules of the DIM-containing pharmaceutical composition twice a day, and Group II (16 patients) were given 2 capsule of the crystalline DIM pharmaceutical composition twice a day.

TABLE 3

Pharmacokinetics of DIM in various compositions

| Group | Composition | $C_{max}$ [µg/mL] | Ratio $C_{max}$ composition/control | $AUC_{0-24\,h}$ [µg·h/mL] | Ratio $AUC_{0-24\,h}$ composition/control |
|---|---|---|---|---|---|
| 1 | Control (0.5% methyl-cellulose) | 0.22 ± 0.02 | | 3.88 ± 0.08 | |
| 2 | L10/F127 (Example 3) | 4.47 ± 0.17 | 20.3 | 56.76 ± 6.25 | 14.6 |
| 3 | L10/F127 (lyophilically dried, Example 4) | 4.99 ± 0.64 | 22.7 | 58.56 ± 7.76 | 15.1 |
| 4 | F127 (Example 2) | 3.08 ± 0.17 | 14 | 21.55 ± 3.31 | 5.6 |
| 5 | L10 (Example2) | 0.55 ± 0.04 | 2.5 | 7.75 ± 0.32 | 2.0 |

The patients were selected for treatment according to the following criteria:
- outpatients and inpatients with symptomatic and morphologically confirmed PGA and PIN;
- age over 50 years;
- patients who gave written consent and followed doctor's instructions on the treatment prescribed;
- symptom manifestation over 7 on the I-PSS scale;
- $Q_{max}$ over 5 and less than 15 ml/sec.;
- Residual urine not more than 200 ml;
- Prostate volume over 25 cm$^3$.; and
- PSA up to 10 ng/ml.

Assessment of the Effect of the Preparation on Clinical Condition

At the starting point in time (V1), two morphological characteristics, L-PIN and H-PIN, were recorded in both groups. A patient's condition deteriorated, was unchanged, or improved under the effect of the preparation. In all, there were seven possible variants of clinical response within the time interval between V1 and V2. In this case, it is possible to make assessment of the clinical change (between V1 and V2) against the ordinal scale. The Mann-Whitney criterion is the most sensitive of all for comparing clinical change in the group studied.

Figure 3:
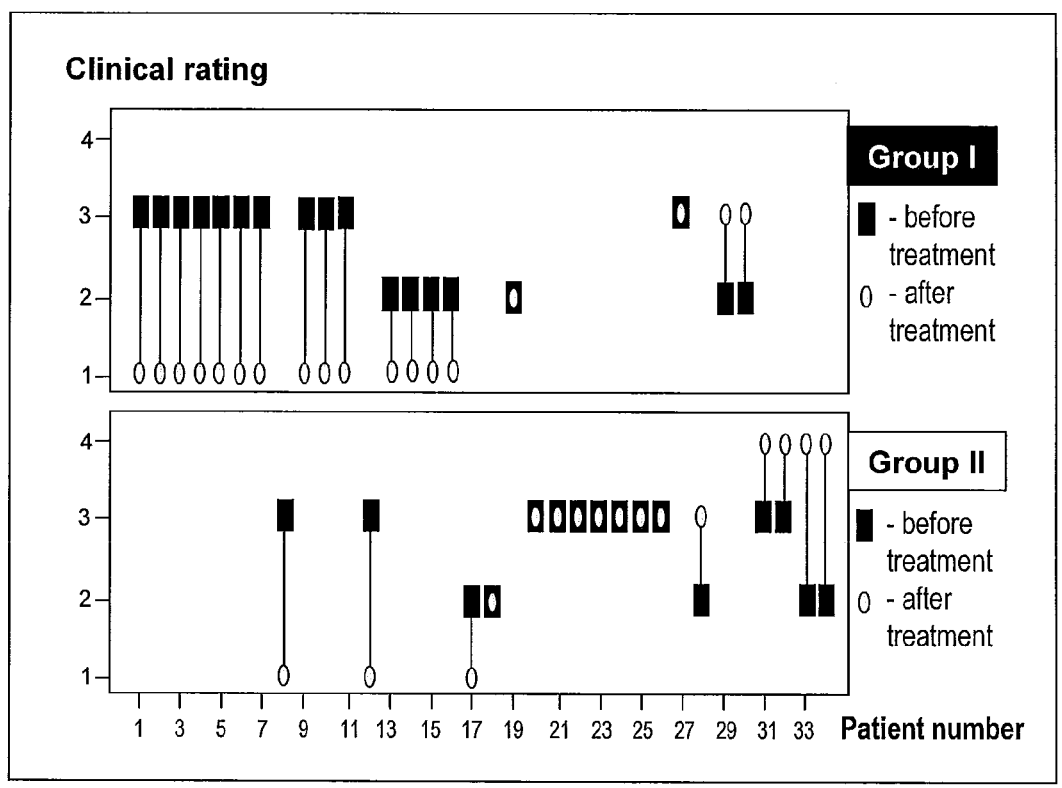
FIG. 3 shows the results of a morphological study of patients with prostate gland adenoma (PGA) and prostate intraepithelial neoplasia (PIN) before and after treatment:
Group I (18 patients) was given the DIM-base pharmaceutical composition in accordance with the invention; and
Group II (16 patients) was given a pharmaceutical composition containing crystalline DIM.

Changes in the morphological study data for all patients are shown in the drawing (see: FIG. 3) that illustrates change in the morphological characteristic in Groups I and II in the course of the study.

On the basis of the dual-sided level of significance of the therapeutic effect, Group I (that was given the DIM-containing pharmaceutical composition according to the invention) and Group II (given a pharmaceutical composition containing crystalline DIM) differed significantly (p=0.002).

Comparison of Malignity Frequency

A separate study was conducted to explore the difference in the malignity frequency in the groups studied. No instances of malignity were observed in the core group (its 18 patients were given the DIM-containing pharmaceutical composition in a new formulation). Four instances of prostate cancer were recorded in the control group (16 patients were given a pharmaceutical composition containing crystalline DIM). Considering a probable error of chi-square approximation, the more accurate Fischer criterion was used.

Conclusion:

The groups studied differed in the frequency of malignity, and their differences were statistically significant (p=0.039).

Figure 4:
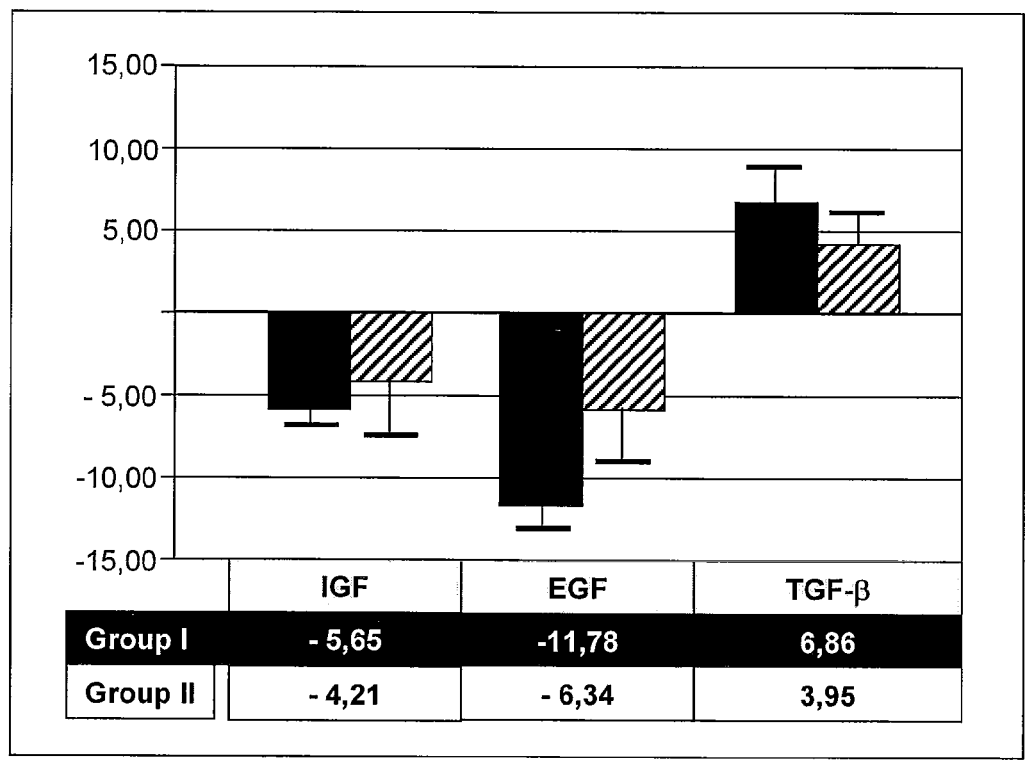
FIG. 4 shows the results of an immuno-histochemical analysis, with IGF and EGF growth factors and TGF-β regulatory factor studied before and after administration of the preparations.

Assessment of the Effect of the Claimed DIM-containing Pharmaceutical Composition on Immuno-histochemical Data:

An immuno-histochemical analysis was carried out in two groups of four patients each from Group I given the DIM-containing pharmaceutical composition in a new formulation and Group II that received a pharmaceutical composition containing crystalline DIM, respectively. Assessment was made of factors such as IGF and EGF growth factors and TGF-β regulation factor before and after administration of the preparations studied. The starting values of IGF, EGF and TGF-β being statistically uniform, the following differences in the level of these parameters were recorded upon further measurement:

A statistically reliable decrease in the growth factors IGF (p=0.004) and EGF (p=0.002) was recorded, as also was an increase in the level of TGF-β (p=0.047) in the group of patients taking the DIM-containing pharmaceutical composition in a new formulation. No reliable dynamics were registered in the control group. The data obtained are shown graphically in the drawing below (see: FIG. 4).

Conclusion

The data obtained for a reliable decrease in the IGF and EGF growth factors and an increase in the TGF-β level in the group of patients taking the claimed DIM-containing pharmaceutical composition point to the effect of the active agent of the preparation on the principal signaling mechanisms of pathological cellular proliferation, and also to the induction of apoptosis of transformed cells.

No side effects or undesirable events were registered during treatment.

The DIM-containing pharmaceutical composition in a new formulation shows an anti-proliferative activity in patients with prostate gland adenoma and prostate intraepithelial neoplasia.

The DIM-containing pharmaceutical composition in a new formulation is a safe drug to treat PGA and PIN because it had no side effects and undesirable events during the treatment period.

The invention claimed is:

1. A pharmaceutical composition for peroral administration comprising 3,3'-diindolylmethane
    a first block copolymer of oxyethylene and oxypropylene, wherein the content of the oxypropylene block is less than 30 mass % and the molecular mass of the oxyethylene block is 4,000 Da and
    a second, different block copolymer of oxyethylene and oxypropylene, in which the content of the oxypropylene block is 60 mass % and the molecular mass of the oxyethylene block is 3,200 Da,
    wherein a ratio of said first block copolymer to the 3,3'-diindolylmethane is from 2:1 to 10:1.

2. The pharmaceutical composition as claimed in claim 1, further containing a pharmaceutically acceptable carrier.

3. The pharmaceutical composition as claimed in claim 2, said composition being in the form of a tablet, lyophilized powder, suspension, or capsule.

* * * * *